United States Patent [19]

Richter

[11] Patent Number: 4,950,161

[45] Date of Patent: Aug. 21, 1990

[54] ASSEMBLY FOR CONNECTING A CROWN PART TO AN IMPLANT

[76] Inventor: Ernst-Jürgen Richter, Schlossparkstrasse 56, 5100 Aachen, Fed. Rep. of Germany

[21] Appl. No.: 359,959

[22] Filed: Jun. 1, 1989

Related U.S. Application Data

[63] Continuation-in-part of Ser. No. 247,110, Sep. 19, 1988, abandoned.

[30] Foreign Application Priority Data

Sep. 17, 1987 [DE] Fed. Rep. of Germany ....... 3731265

[51] Int. Cl.$^5$ .............................................. A61C 8/00
[52] U.S. Cl. ..................................... 433/169; 433/173
[58] Field of Search ............... 433/169, 173, 174, 175, 433/176, 201.1

[56] References Cited

U.S. PATENT DOCUMENTS

| 2,880,508 | 4/1959 | Lester et al. | 433/169 |
| 4,014,095 | 3/1977 | Heimansohn | 433/169 |
| 4,318,696 | 3/1982 | Kasama et al. | 433/169 |
| 4,552,532 | 11/1985 | Mozsary | 433/173 |
| 4,609,354 | 9/1986 | Koch | 433/173 |
| 4,657,510 | 4/1987 | Gittleman | 433/173 |
| 4,746,293 | 5/1988 | Lundgren et al. | 433/169 |

FOREIGN PATENT DOCUMENTS

3325666 of 0000 Fed. Rep. of Germany ..

Primary Examiner—John J. Wilson
Attorney, Agent, or Firm—Herbert Dubno

[57] ABSTRACT

An assembly for connecting a crown part to an implant in which the jaw of an individual has an implant-connecting member in which a setscrew extends into a pin of the crown-connecting part, the two members having juxtaposed surfaces which are in continuous and all-around sealing adhesive-bonding relationship with an annular disk cushion permitting relative displacement of the crown connector to the implant coupler.

13 Claims, 1 Drawing Sheet

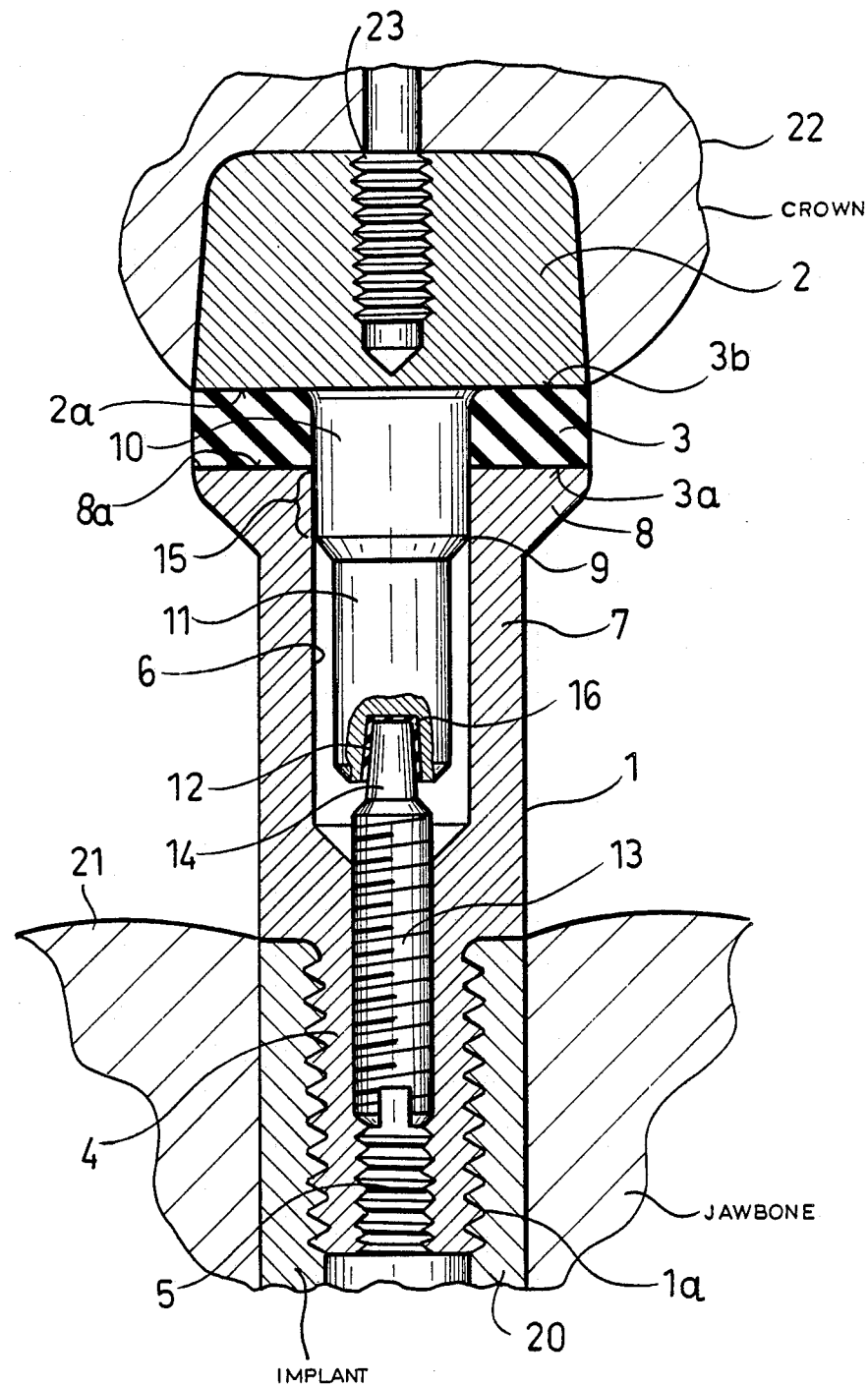

ASSEMBLY FOR CONNECTING A CROWN PART TO AN IMPLANT

CROSS REFERENCE TO RELATED APPLICATION

This application is a continuation-in-part of Ser. No. 07/247,110 filed Sept. 19, 1988, now abandoned.

FIELD OF THE INVENTION

My present invention relates to an assembly for connecting a crown part to an implant and, more particularly, to a crown fastening device for the attachment of a crown or a prosthesis equivalent to a crown to an implant in the jaw of an individual.

More particularly the invention relates to an assembly for the attachment of a prosthetic crown part to an implant of the type which comprises a coupling member connected with the implant, a connecting member connected with the crown and a cushion or buffer member of an elastic material adapted to act as a shock damper.

BACKGROUND OF THE INVENTION

Implant systems using an elastic cushion are known in which an implant body in the jaw of the patient has an elastic cushion member, namely, a so-called intramobile element, screwed into it and composed of a synthetic resin material. This intramobile element generally has the form of a cylindrical bushing or boss. The cushioning element is surrounded by a spacing sleeve which is braced on the one hand upon the implant body and on the other hand on a flange on the upper end of the intramobile element. In a central threaded bore of the cushion element, a so-called implant post is threaded and serves to attach the connecting member of the crown to the implant structure. This connecting member can have a threaded pin which can be screwed into an internal thread of the implant post.

This known implant system has the drawback that, upon deformation of the elastic member in the radial direction, gaps and/or microscopic hollow spaces are formed which can become filled with contaminants and enable bacteria to establish themselves in the peri-implant region with the result that the gum tissue around the implant becomes unstable and the tissue which, under the most desirable conditions should reform and develop actively around the implant, does not.

On a long term basis this can lead to infection, bone loss and even destructive loss of the implant and hence the prosthesis.

While it may be conjectured that placing the elastic member under a certain degree of prestress would suffice to prevent the development of gaps and the like with negative results, in practice it is found that this approach does not reliably eliminate the problem since the prestress cannot be maintained because of the natural creep of the elastic synthetic resin material.

OBJECTS OF THE INVENTION

It is, therefore, the principal object of the present invention to provide an improved implant/crown fastening assembly for a prosthetic attachment in the jaw of a patient which can eliminate the aforedescribed drawbacks.

More specifically, it is an object of my invention to provide an assembly for the purposes described which is not only simple to apply and use, has a long life without the development of infection or bone deterioration and like disadvantages, but practically excludes the formation of radial gaps and microhollows or crevices even with the most intensive use.

SUMMARY OF THE INVENTION

These objects and others which will become apparent hereinafter are attained in accordance with the invention by providing the elastic cushion at least in regions of its outer contact surfaces with an adhesive bond to the juxtaposed end faces of the coupling member connected to the implant and the connecting member joined to the crown so that it is fixedly connected to these end faces at least in the outermost regions and all around the periphery of each contact region.

The bonding can be effected in various ways including vulcanization, adhesive bonding or cementing, injection molding, or the like.

In this manner I am able to completely exclude the formation of cracks, gaps and even microcrevices and the like in a reliable manner even upon application of heavy compressive forces on the prosthesis.

In spite of the fixed connection of the elastic cushion with the coupling member and the connecting member, the resiliently yieldable characteristic is maintained and the desired effect can occur in both the axial and orthogonal directions. In general, the assembly can have the two-stage mobility which has been considered in the past to be important in the mounting of a crown.

More specifically, the assembly can comprise:

an implant-connecting member affixed to an implant and having an end face turned away from the implant;

a crown-part-connecting member adapted to be affixed to the prosthetic crown part and having an end face juxtaposed with the end face of the implant-connecting member; and an elastic cushion interposed between the members and being, at least in regions of outer surfaces thereof in contact with the end faces, being fixedly connected to the end faces.

Advantageously, the elastic cushion is an annular disk and preferably the implant-connecting member is elongated and formed on an end opposite its end face an end portion provided with a threaded bore opening into a cylindrical recess of larger diameter than the bore and interposed between the end face of the implant-connecting member and the bore, the end portion having a smaller diameter than another end portion of the implant-connecting member formed with the recess and the end face of the implant-connecting member.

The other end portion can be provided with an enlargement extending outwardly and defining the end face of the implant-connecting member and the annular disk can be bonded to the end face of the latter member over the entire area of this enlargement. Advantageously, the crown-part-connecting member is formed with a pin projecting axially from the end face of the crown-part-connecting member, traversing the annular disk and extending into the cylindrical recess.

This pin can be stepped so as to have a large-diameter step adjacent the end face of the crown-connecting member and a small-diameter step adjoining the large-diameter step. The small-diameter step has an inwardly tapered frustoconical recess receiving the complementary head, with interposition of an elastic layer, of a setscrew threaded into the aforementioned bore.

BRIEF DESCRIPTION OF THE DRAWING

The above and other objects, features and advantages of the present invention will become more readily apparent from the following description, reference being made to the accompanying drawing, the sole FIGURE of which is a cross-sectional view through an assembly according to the invention.

SPECIFIC DESCRIPTION

In the drawing there is a connecting member 1 which can be threaded via a screw thread 1a into the bore of the jaw of a patient or into an implant 20 previously inserted into the jaw bore 21.

On the crown, a crown-connecting member 2 can be fastened and between the members 1 and 2 can be provided a cushion 3 of an elastic synthetic resin. This cushion is in the form of an annular disk and is preferably composed of an elastomer.

The outer contact surfaces 3a and 3b of this disk which engage the end faces 8a and 2a of the members 1 and 2 over the entire areas thereof are bonded fixedly together with a continuous adhesive contact, by, for example, vulcanization, adhesive bonding or the like.

Because of this fixed connection of these three parts, a radial gap formation between them as well as the formation of microcavities for the accumulation of materials which can support bacteria is reliably excluded and there is no danger of the penetration of bacteria and other contaminants into the 15 assembly.

The end portion 4 of the connecting member 1 is provided with an internally threaded bore 5 opening upwardly into a cylindrical recess 6 of larger diameter, the portion 4 itself being of a smaller diameter than the other end portion 7 of the connecting member 1.

This larger-diameter portion of the connecting member 1 is provided at its free end with an outwardly extending enlargement 8 defining the end face 8a which abuts and is adhesively bonded to the surface 3a of the annular disk cushion 3.

On the implant side, the connecting member 2 is formed unitarily with an axially extending pin 9 passing through the annular disk cushion 3 and extending into the cylindrical recess 6.

The pin 9 is stepped and comprises a large-diameter step 10 which is cylindrical and merges via a frustoconical transition portion with a small-diameter step 11. The free end of the pin 9 is formed with an axially inwardly tapered recess 12.

In the internally threaded bore 5 of the coupling member 1, a setscrew 13 can be screwed and has at its upper end a head 14 which is free from a thread and is frustoconically tapered in the direction of the crown so as to be complementary to the recess 12.

Between the uppermost portion of the large-diameter step 10 of the pin 9 and the surrounding region of the recess 6, a tolerance fit is provided. The region of this tolerance fit has been represented at 15 in the drawing.

Between the bottom of the recess 12 of pin 9 and the sides of the head 14 of the setscrew 13, an elastic layer 16 can be provided.

The conical recess 12 serves as a stop for the axial and orthogonal deflection of the crown relative to member 1 since a slight play is provided between the head 14 and the recess 12 of the pin. This is adjustable by varying the position of the setscrew and hence of the head 14. Thus the device of the invention has an adjustable stop to the permitted mobility.

The degree of axial shiftability of the crown connector 2 relative to the coupling member 1, therefore, is set by adjustment of the setscrew. The orthogonal shiftability which is permitted initially is a consequence of a lateral movement of the crown connector 2 out of the centering position of the cushion 3 until the tolerance fit in the region 15 causes the pin 9 to abut the wall of the recess 6.

Between the crown connector 2 and the coupling member 1 there are no friction or stress-transmission effects because relative motion is taken up by the elastic member 3 which is bonded to the confronting surfaces.

The elastic material which is selected for member 3 should, of course, be sufficient to withstand various relative movements and both the axial and orthogonal loads while retaining sufficient restoring force. Silicone rubbers have been found to be effective for this purpose.

Dimensions of the second phase of the axial mobility are established by the dimensions of the regions 10 and 11 of the pin 9 and the head 14 of the setscrew, this being compressed by axial loading and providing the elastic resistance to such loading.

The dimensions of the second phase of the orthogonal deflection can be provided by selection of an appropriate length of the pin 9 and the diameter of the latter since both of these factors control the bending characteristics when, of course, the material from which the pin is constituted is taken into account.

The crown-fastening device of the invention has a hollow internal space which allows the two-stage mobility in the axial and orthogonal directions but which is completely sealed by the cushion 3 and the fact that it is continuously bonded to both the end face of the coupling member and the end face of the crown connector 2.

The crown 22 is attached to the crown connector 2 by a screw (not shown) threaded into the bore 23 in the crown connector.

I claim:

1. A jaw-implant connecting assembly for affixing a prosthetic crown part to a jaw implant, said assembly comprising:
    an implant-connecting member having first and second end portions at opposite termini thereof, said member being affixed to an implant and having an and face on said first end portion turned away from said implant;
    a crown-part-connecting member adapted to be affixed to said prosthetic crown part and having an end face juxtaposed with said end face of said implant-connecting member;
    an elastic cushion which is an annular disk interposed between said members and, at least in regions of outer surfaces thereof in contact with said end faces, being fixedly connected to said end faces; and
    wherein said implant-connecting member is elongated, said second end portion is provided with a threaded bore opening into a cylindrical recess of larger diameter than said bore and interposed between said end face of said implant-connecting member in said bore, said second end portion having a smaller diameter than said first end portion.
2. The assembly defined in claim 1 wherein said first end portion is provided with an enlargement extending outwardly from said second end portion and defining the end face of said implant-connecting member.

3. The assembly defined in claim 2 wherein said annular disk is bonded to said end face of said implant-connecting member over the entire area thereof and of said enlargement 4. The assembly defined in claim 2 wherein said crown-part-connecting member is formed with a pin projecting axially from said end face of said crown-part-connecting member, traversing said annular disk and extending into said cylindrical recess.

5. The assembly defined in claim 4 wherein said pin is stepped so as to have a large-diameter step adjacent the end face of said crown-part-connecting member and a small-diameter step adjoining said large-diameter step.

6. The assembly defined in claim 5 wherein said pin has a free end provided with an axially inwardly extending recess.

7. The assembly defined in claim 6 wherein said axially inwardly extending recess is inwardly conically tapered.

8. The assembly defined in claim 7 wherein said cylindrical recess and said large-diameter step are dimensioned so that said large-diameter step is received with a tolerance fit in said cylindrical recess.

9. The assembly defined in claim 7, further comprising a setscrew threadedly received in said bore and having a head extending into said inwardly extending recess.

10. The assembly defined in claim 9 wherein said head has a shape complementary to that of the inwardly extending recess.

11. The assembly defined in claim 10 wherein said head is received with a slight play in said inwardly extending recess.

12. The assembly defined in claim 11, further comprising an elastic layer between the bottom of said inwardly extending recess and said head.

13. A jaw-implant connecting assembly for affixing a prosthetic crown part to a jaw implant, said assembly comprising:
- an implant-connecting member having first and second end portions at opposite termini thereof, said member being affixed to an implant and having an end face on said first end portion turned away from said implant;
- a crown-part-connecting member adapted to be affixed to said prosthetic crown part and having an end face juxtaposed with said end face of said implant-connecting member;
- an elastic cushion which is an annular disk interposed between said members and, at least in regions of outer surfaces thereof in contact with said end faces, being fixedly connected to said end faces; and
- wherein said implant-connecting member is elongated, said second end portion is provided with a threaded bore opening into a cylindrical recess of larger diameter than said bore and interposed between said end face of said implant-connecting member in said bore, said second end portion having a smaller diameter than said first end portion;
- said first end portion is provided with an enlargement extending outwardly from said first end portion and defining the end face of said implant-connecting member;
- said annular disk is bonded to said end face of said implant-connecting member over the entire area thereof and of said enlargement;
- said crown-part-connecting member is formed with a pin projecting axially from said face of said crown-part-connecting member, traversing said annular disk and extending into said cylindrical recess;
- said pin is stepped so as to have a large-diameter step adjacent the end face of said crown-part-connecting member and a small-diameter step adjoining said large-diameter step;
- said pin has a free end provided with an axially inwardly extending recess;
- said cylindrical recess and said large-diameter step are dimensioned so that said large-diameter step is received with a tolerance fit in said cylindrical recess; and
- a setscrew is threadedly received in said bore and has a head extending into said inwardly extending recess.

* * * * *